United States Patent

Reuss et al.

[11] Patent Number: 5,858,379
[45] Date of Patent: Jan. 12, 1999

[54] ADHESIVE FOR DENTAL PROSTHESIS

[75] Inventors: Mira Reuss, Mannheim; Rainer Knollman, Herford, both of Germany

[73] Assignee: Reckitt & Colman Inc., Wayne, N.J.

[21] Appl. No.: 549,698

[22] PCT Filed: May 13, 1994

[86] PCT No.: PCT/EP94/01557

§ 371 Date: Oct. 21, 1996

§ 102(e) Date: Oct. 21, 1996

[87] PCT Pub. No.: WO94/26232

PCT Pub. Date: Nov. 24, 1994

[30] Foreign Application Priority Data

May 13, 1993 [DE] Germany ............... 43 16 115.4

[51] Int. Cl.$^6$ ............... A61K 9/00; A61F 13/00
[52] U.S. Cl. ............... 424/401; 424/434; 424/435
[58] Field of Search ............... 424/400, 401, 424/422, 434, 435

[56] References Cited

U.S. PATENT DOCUMENTS 4,495,314  1/1985  Keegan ............... 523/120
5,024,701  6/1991  Desmarais ............... 106/35

FOREIGN PATENT DOCUMENTS 0140486  7/1984  European Pat. Off. .

OTHER PUBLICATIONS

Hansen & Rosenthal, Pionier® PLW Salben–Cremegrundlage, 1989, Hamburg, Germany.

*Primary Examiner*—Thurman K. Page
*Assistant Examiner*—Kathryne E. Shelborne
*Attorney, Agent, or Firm*—Fish & Richardson P.C.

[57] ABSTRACT

The use of a hydrophobic oleogel of essentially temperature-independent viscosity and consistency as a carrier base substance in an adhesive for dental prostheses is disclosed. The hydrophobic oleogel here is preferably a viscous paraffin in combination with amorphous polyethylene, with physical properties resulting from its preparation.

15 Claims, 4 Drawing Sheets

ADHESIVE FOR DENTAL PROSTHESIS

The invention relates to an adhesive for dental prostheses.

Adhesives for dental prostheses are used to match dentures to the mucous membrane of the soft parts of the palate and to the gingival furrows with a tight and adhering fit, or at least to improve the match. The adhesive is applied to the denture, which is then inserted in the mouth. Saliva moistens the surface of the adhesive layer and in this way causes the adhesive to swell, which also develops the adhesive force.

The adhesive strength and duration of adhesion are decisive parameters. The mechanisms which are responsible for the holding action are highly complex. The viscosity of the carrier base substance and as a consequence of the finished product play an important role. Carrier base substances which are used are, inter alia, paraffin oil, Vaseline (petrolatum), waxes etc., which are diluted with polyethylene glycol, glycerol or the like as required and make up about 20 to 60% of the finished product in total. When compiling the formula, efforts are made to provide a medium for the crevice space which has as constant as possible an action and likewise constant flow properties.

The viscosity is primarily determined by the overall formula, that is to say by the active compounds and carriers in their entirety in the adhesive. There are a large number of compositions, each of which are adapted to various applications.

For example, DE-A 21 33 709 discloses a process for the preparation of an adhesive cream for dental prostheses in which a strong adhesive force is achieved by drying the adhesive very homogeneously to a moisture content of 10%±1% and then comminuting it to a fineness of 50 um.

The problem of removing an adhesive from denture plates, where furthermore it should be possible to press this adhesive out of a tube without applying great force, is solved according to DE-A 37 15 100 by using a resin of low softening point which is chosen from polyvinyl acetate resins and naturally occurring chichle gum and comprises at least one compound having one or more polyoxypropylene groups.

EP-A 0 073 850 proposes providing the adhesive substances at least partly with a coating which dissolves only slowly in saliva. As a result, the adhesive strength is retained over a long period of time, since any adhesive substances rinsed out by saliva are replaced by those from which the coating has just been dissolved.

EP-A 0 122 481 proposes an adhesive which comprises a mixture of copolymers of alkyl vinyl ether/ maleic anhydride salts, for example 3Ca:1Na, and sodium carboxymethyl-cellulose with a carrier of a paraffin oil which has been thickened with polyethylene having a low molecular weight in the range from 1,000 to 21,000. An adhesive which has considerably improved adhesive properties at an oral temperature of 37° C. is thus provided.

In addition to creamy and gelatinous adhesives, liquid adhesives have also been developed, in particular those based on paraffin oil, as disclosed, for example, in U.S. Pat. No. 4,280,936. Such adhesives present, in particular, the problem of being washed out by saliva on the one hand and by drinks on the other hand. It has been proposed to use sodium carboxymethyl-cellulose and ethylene oxide polymers in a ratio of 3:1. In this procedure, the polyethylene is first mixed into the paraffin oil at a temperature of about 90° C. and the mixture is then cooled to 45° C., after which the sodium carboxymethyl-cellulose is added. The mixture thereby slowly cools further to 35° C. or below.

U.S. Pat. No. 4,542,168 proposes the use of partly neutralized and partly crosslinked polyacrylic acid, to which a hydrophilic polymer is added, in an adhesive. This composition is said to result, in particular, in the adhesive properties being retained for a longer period than usual.

In order to reduce the viscosity of a gel used as the carrier base substance, U.S. Pat. No. 4,495,314 proposes the use of sorbitan monostearate in a content of 0.25 to 2.25% by weight of the gel, in addition to a paraffin oil and a polyethylene wax.

The adhesive properties can be improved if, as proposed in EP-A 0 265 916, zinc salts and strontium salts of certain copolymers are used in combination with salts of ether/maleic anhydride copolymers. The specific viscosity is determined here in a methyl ethyl ketone medium at 25° C.

In the adhesive composition described in EP-A 0 140 486, a hydrophobically modified polymer, for example hydroxyethylcellulose, is employed in order to improve the adhesiveness of compositions which comprise paraffin oil thickened with polyethylene.

It has been found that the viscosity of the known carrier substances is temperature-dependent to a greater or lesser degree. This temperature behaviour is also found in the finished products. Accordingly, the consistency of the adhesives also depends on temperature. The viscosity of the adhesive should remain largely constant in the oral cavity even if the temperature changes considerably due to consumption of cold or hot food. It has not been possible to date to achieve this in a satisfactory manner. Variations in the properties have had to be accepted, since the carrier base substance already showed the undesirable properties.

The object of the invention is to provide an adhesive which has a high viscosity stability and consistency stability at varying temperatures in the mouth, in particular a carrier base substance for adhesives which shows the desired properties and passes these on to the adhesive.

This object is achieved by using a hydrophobic oleogel having an essentially temperature-independent viscosity and consistency as carrier base substance in an adhesive for dental prostheses instead of, for example, Vaseline and/or thickening agents.

A viscous paraffin, if need be having a naphthenic structure, in combination with amorphous polyethylene, which is prepared by a special process, is preferably used as the hydrophobic oleogel.

The paraffin employed is a fraction having a viscosity of about 200 mPa.s (200 cP), that is to say about 240 $mm^2/s$ (240 cSt), at 20° C. (measured by means of a capillary viscometer).

It has been found that the polyethylene should have a molecular weight of more than 80,000, preferably in the range from 80,000 to 130,000, measured by gel permeation chromatography.

The optimum ratio of paraffin to polyethylene, both as described above, is about 93:7 to 97:3, preferably 95:5.

An adhesive for dental prostheses composed of a powder mixture of naturally occurring and/or synthetic active compounds and one or more carrier base substance(s) preferably comprises 30 to 80% by weight, more preferably 30 to 70% by weight, and most preferably 35 to 60%, of the hydrophobic oleogel in its carrier base substance The adhesive should comprise, inter alia, a content of 15 to 35% by weight, preferably 17.5 to 30%, of the hydrophobic oleogel, depending on the desired consistency.

The abovementioned special process, which, in addition to the choice of suitable raw materials, guarantees the quality, is essentially based on heating up the paraffin to above 120° C., for example, to 140° C. (but 160° C. should not be exceeded), and then stirring in and completely dissolving the polyethylene, which takes an after-stirring time of about 4 hours, and at any rate about 2 hours and preferably more than 3.5 hours, at a constant temperature, after which the solution is brought to below room temperature, preferably about 10° C., at a cooling rate of more than 5° C./second, for example 6° C./second.

As a result of the process just described, that is to say complete, permanent solubilisation at a very high temperature and very rapid cooling, a gel is formed which has a particularly fine molecular structure and the possibility of practically unrestricted migration of the active compounds, chiefly caused by the formation and presence, in this case only, of exclusively amorphous polyethylene distributed very finely and uniformly in the combination, without crystalline or granular regions visible under a polarization microscope.

The adhesive thereby acquires, via the carrier substance, a consistency which approximately corresponds to that when Vaseline is used, but moreover exhibits the high diffusion and migration capacity already described and is influenced only a little by variations in temperature, even in the wide range of between 5° C. and 70° C., during the incidences which occur in practice in the dental prosthesis sector. In the more relevant range of 10° C. to 55° C., the influence of temperature on the viscosity and consistency is minimal in practice. A more constant, longer and higher adhesive action is guaranteed by the favourable temperature stability. This hydrophobic oleogel has not hitherto been used in adhesives for dental prostheses.

The molecular structure desired, with exclusively amorphous polyethylene, is obtained particularly reliably if the polyethylene is dissolved in the paraffin at 150° C. and the solution is then subsequently stirred for four hours. The very rapid cooling proceeds particularly reliably at a cooling rate of at least 6° C./second.

The polyethylene concentration has also been optimized via the recognized values and parameters for structural stability in vitro and in vivo. Given the quality characteristics as mentioned above, only an about 5% strength oleogel is to be employed for the adhesives for dental prostheses.

Using the raw materials thus chosen and this process, without thickening or admixing of any other substances, an oleogel, respectively, having a particularly fine, homogeneous microstructure without crystalline or granular regions is obtained. The stability of this structure resulting furthermore from the amorphous form of the polyethylene is particularly advantageous. The finished product, adhesive gel or cream, does not "oil" out, which means that a long-term stability, without separation of liquid paraffin, is also ensured.

A matrix for the active compounds of adhesives for dental prostheses is thus available which has a constant viscosity and consistency during use, even in the temperature range which is occasionally wide in practice, and which at the same time displays unrestricted migration and unchanged structural viscosity in deep-lying layers and as a consequence no flow limit and no sedimentation.

In the following examples, several constituents are indicated by their tradenames:

The hydrophobic oleogel having the desired properties for the adhesives for dental prostheses is a paraffin hydrocarbon having no aromatic fractions; it is called "PLW" below and is marketed under "Pionier$^{(R)}$ PLW" by Hansen & Rosenthal, Hamburg, Germany. Up to now it has been used in ointment.

Gantrez (supplier: ISP Europe, Guildford, Surrey, England) consists of mixed Na/Ca salts of the copolymer of methyl vinyl ether/maleic anhydride.

Polyox$^{(R)}$ Water-Soluble Resins (supplier: Union Carbide Chemicals and Plastics Company Inc., Bound Brook, N.J.) are non-ionic water-soluble poly(ethylene oxide) polymers supplied in a variety of viscosity grades. The degree of polymerization, n, varies from about 2,000 to about 180,000, depending on the vicosity grade of resin. The common structure is $-(OCH_2CH_2)_n OH$.

Walocel$^{(R)}$CRT products (supplier: Wolff Walsrode AG, Walsrode, Germany) are suitable for use as carboxymethyl-cellulose components, they are available in a highly viscous and a medium viscous mode and consist of purified sodium carboxymethyl-cellulose.

EXAMPLE 1

Gantrez and/or Polyox with a content of 32% by weight in the finished product are admixed to a content of 32% by weight of paraffin oil in a mixer, and 17,5% by weight of PLW furthermore are added. The mixture is then topped up with 18% of carboxymethyl-cellulose and/or alginate in a manner which is known per se. A product which has a viscosity of about 3000 mPa.s (3000 cP) at 10° C. and even at 70° C. reaches about 250 mPa.s (250 cP), that is to say still has creamy properties, is obtained.

EXAMPLE 2

The following amounts by weight are employed in the same sequence as in Example 1.29% of Gantrez and/or Polyox are added to 31.5% of paraffin oil, as well as 18.5% of PLW and 21% of carboxymethyl-cellulose and/or alginate. A similar, relatively uniform course of the viscosity over the temperature range from 10° C. to 70° C. is also achieved here.

EXAMPLE 3

29% by weight of Gantrez and/or Polyox and 21% by weight carboxymethyl-cellulose and alginate as in Example 2 are added to 25% of paraffin oil, but the content of PLW is now 25%. As before, uniform viscosity properties are obtained over the entire temperature range stated.

EXAMPLE 4

With otherwise the same amounts of weight as in Example 3, very low amounts of Vaseline are added, to this part replacing the carrier base substance according to the invention. As result, up to 5% Vaseline could be added without degrading the improved characteristics of the adhesive.

Comparison Example

With otherwise the same amounts by weight as in Example 3, 12% of Vaseline is used instead of the carrier base substance according to the invention and the content of paraffin oil is 38%.

The shear properties of the substances are investigated and compared in a Rheomat of the Contraves 115 or Contraves TV type.

Figure 1:
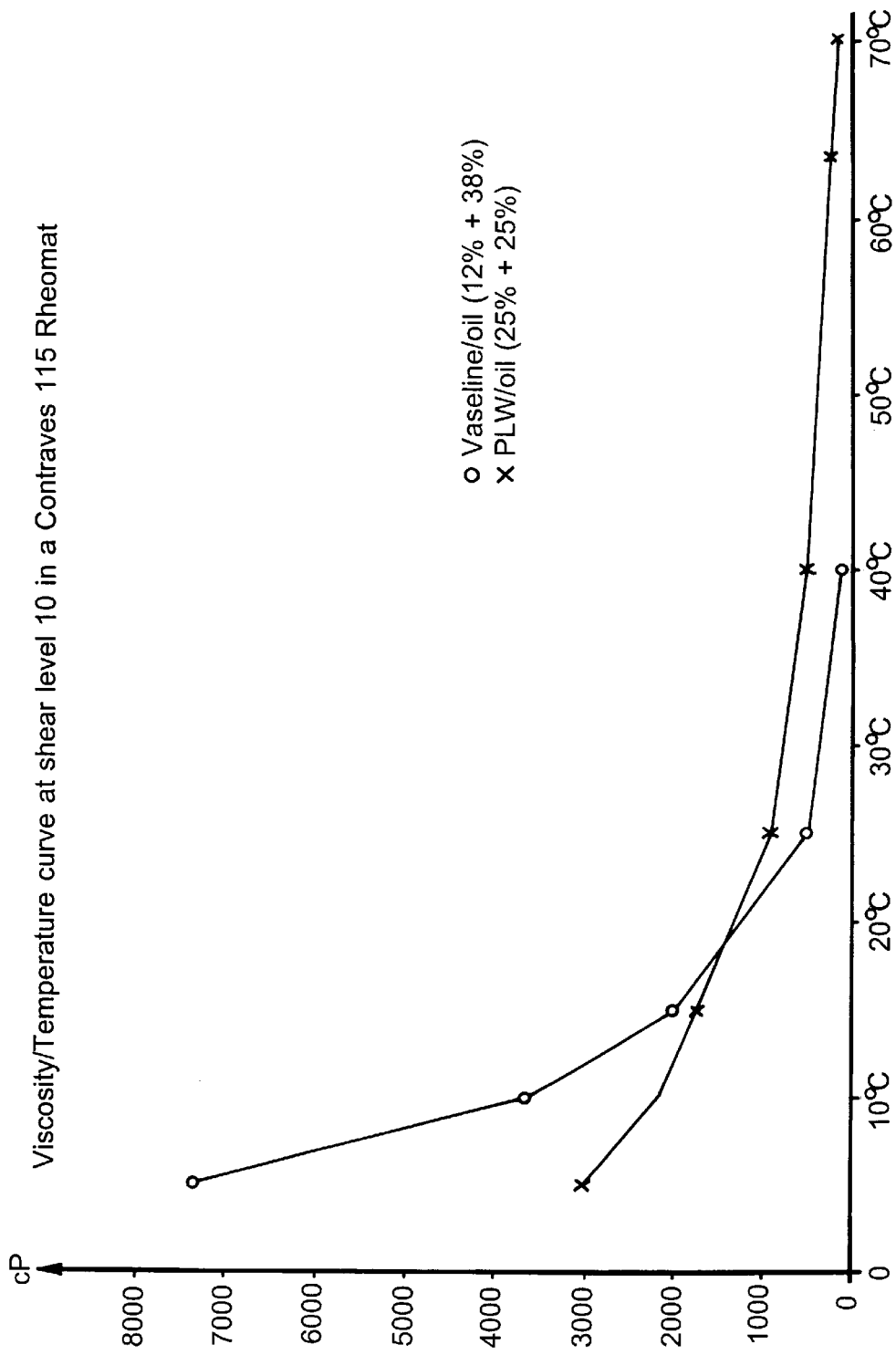
FIG. 1 shows the viscosity/temperature curve at shear level 10.

FIG. 1 shows the viscosity properties as a function of temperature at shear level 10. Conventional carrier base substance based on Vaseline/paraffin oil in the formula according to the comparison example shows a viscosity at 5° C. of about 7300 mPa.s (7300 cP), this value falls to 3600 mPa.s (3600 cP) at 10° C., and subsequently falls in an approximately exponential course to virtually 0 at 40° C. On the other hand, a carrier base substance according to Example 3 shows a very uniform course in the viscosity as a function of temperature. The viscosity is only 3000 mPa.s (3000 cP) at 5° C., falls to about 2200 mPa.s (2200 cP) at 10° C., and then continues to fall slowly to assume 500 mPa.s (500 cP) at 40° C., and even at 70° C. still reaches a value of 250 mPa.s (250 cP)

Figure 2:
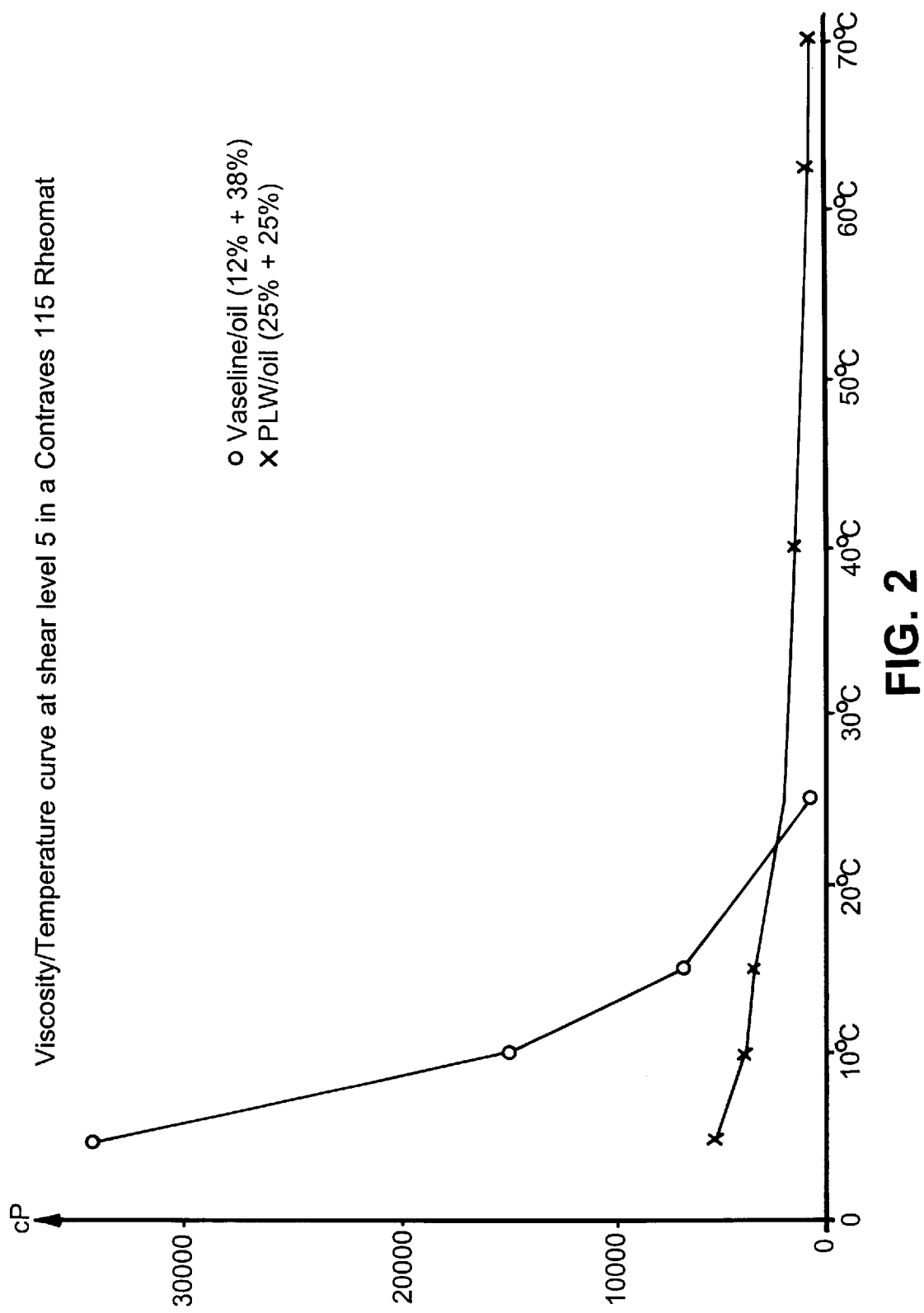
FIG. 2 shows the viscosity/temperature curve at shear level 5.

FIG. 2 shows the properties under otherwise identical conditions at shear level 5. The conventional carrier base substance has a viscosity value of 34,000 mPa.s (34,000 cP) at 5° C., and at 25° C. this value has fallen to below 1,000 mPa.s (1,000 cP). The carrier base substance according to Example 3 has a viscosity of only slightly above 5,000 mPa.s (5,000 cP) at 5° C., this value falls to above 2,000 mPa.s (2,000 cP) at 25° C., and is still about 500 mPa.s (500 cP) at 70° C.

Figure 3:
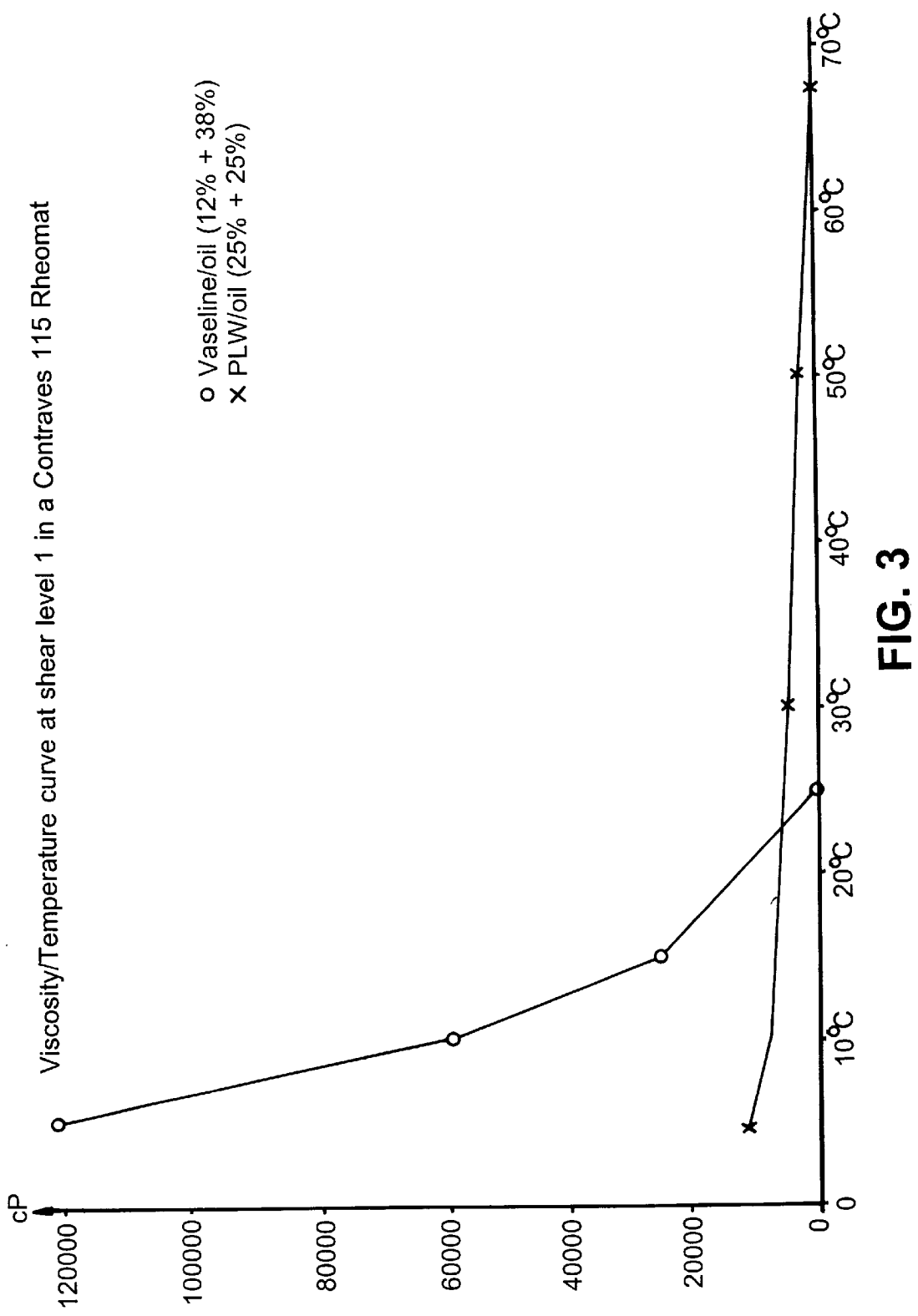
FIG. 3 shows the viscosity/temperature curve at shear level 1.

FIG. 3 shows the circumstances at shear level 1, where the conventional carrier base substance drops from 120,000 mPa.s (120,000 cP) at 5° C. to 0 at 25° C. The carrier base substance from Example 3 according to the invention has a viscosity of approximately 10,000 mPa.s (10,000 cP) at 50° C., which drops relatively slowly and is about 3,000 mPa.s (3,000 c) at 30° C., still about 1,500 mPa.s (1,500 cP) at 50° C., and falls to 0 only at 70° C.

Figure 4:
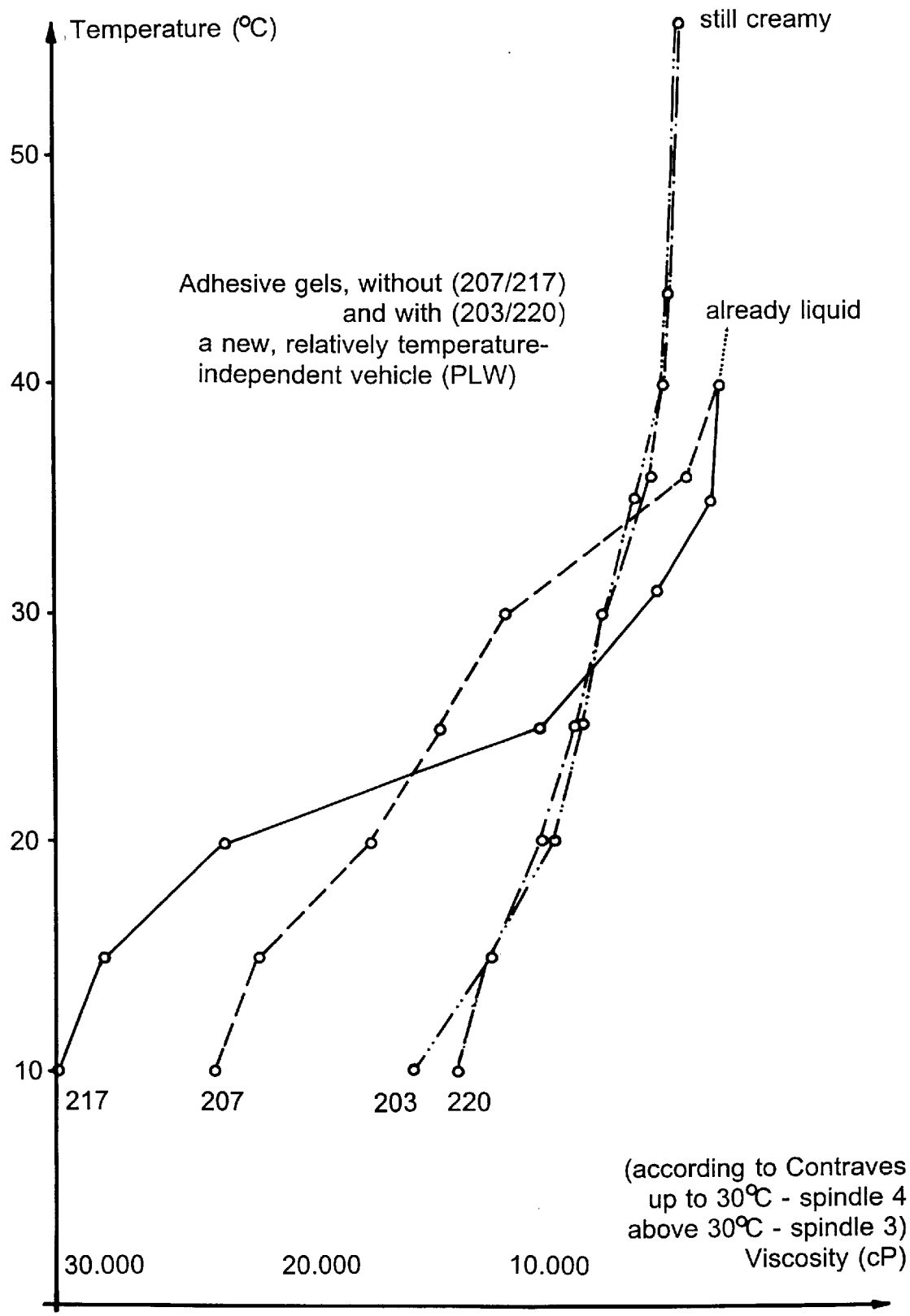
FIG. 4 shows temperature/viscosity curves of conventional adhesive gels as well as of adhesive gels according to the present invention.

FIG. 4 compares the temperature/viscosity properties of adhesive gels, the curves labelled 207 and 217 representing known recipes based on Vaseline, and curves 203 and 220 representing those in which the carrier base substance according to the invention has been used.

In the case of the conventional adhesive gels, in particular adhesive gel 217, the viscosity falls sharply as the temperature rises, a value of 30,000 mPa.s (30,000 cP) being obtained in adhesive gel 217 at 10° C. and a value of 23,000 mPa.s (23,000 cP) being obtained in adhesive gel 207. Both gels are liquid at 40° C., that is to say a viscosity of 0 mPa.s (0 cP) is measured. By comparison, adhesive gels 203 and 220 show hardly any change in viscosity in the temperature range under consideration. At 10° C., the two adhesive gels have a viscosity in the range from 12,000 to 15,000 mPa.s (12,000 to 15,000 cP), and this does not drop below 2,000 mPa.s (2,000 cP) even at a temperature of virtually 60° C. The adhesive gel is still creamy even at these high temperatures.

The adhesive creams and adhesive gels investigated comprise about 50% of active compounds and 50% of carrier base substance in their formula.

A largely constant consistency can also be achieved at varying temperatures with adhesives which use the new carrier base substance, even when very cold or very hot drinks or food are consumed, leading to a constant adhesive action in the course of the daytime use sought.

The features of the invention which are disclosed in the above description, the drawing as well as the claims can be essential, both individually and in any desired combination, for realization of the invention in its various embodiments.

We claim:

1. An adhesive for a dental prosthesis comprising a hydrophobic oleogel characterized as having a temperature-independent viscosity and consistency as a carrier base substance of the adhesive, wherein said hydrophobic oleogel comprises a paraffin having a viscosity of about 200 Pa.s, and amorphous polyethylene having a molecular weight of at least 80,000.

2. The adhesive for a dental prosthesis according to claim 1, characterized in that:
   the paraffin and polyethylene are provided in a ratio of about 93:7 to 97:3.

3. The adhesive for a dental prosthesis according to claim 1, characterized in that:
   the carrier base substance has a weight content of 30 to 80% of hydrophobic oleogel.

4. The adhesive for a dental prosthesis according to claim 1, characterized in that:
   the adhesive has a weight content of about 15 to 35% of hydrophobic oleogel.

5. The adhesive for a dental prosthesis according to claim 1, wherein the hydrophobic oleogel is prepared by dissolving the polyethylene in the paraffin at above 120° C., subsequently stirring in the mixture for at least two hours, and cooling the solution to below room temperature at a cooling rate of more than 5 C./second.

6. The adhesive for a dental prosthesis according to claim 5, wherein the hydrophobic oleogel is prepared by dissolving the polyethylene in the paraffin at about 150° C., subsequently stirring the mixture for about 4 hours and cooling the solution to about 10° C. at a cooling rate of about 6 C./second.

7. The adhesive for a dental prosthesis according to claim 5 wherein the hydrophobic oleogel is prepared by dissolving the polyethylene in the paraffin at a temperature not higher than 160° C.

8. The adhesive for a dental prosthesis according to claim 1 characterized in that:
   the molecular weight of the polyethylene is in the range of 800,000 to 130,000 measured by gel permeation chromatography.

9. The adhesive for a dental prosthesis according to claim 2 characterized in that:
   the paraffin and polyethylene are provided in a ratio of about 95:5.

10. The adhesive for a dental prosthesis according to claim 3 characterized in that:
   the carrier base substance has a weight content of 30 to 70% of a hydrophobic oleogel.

11. The adhesive for a dental prosthesis according to claim 3 characterized in that:
   the carrier base substance has a weight content of 35 to 60% of a hydrophobic oleogel.

12. The adhesive for a dental prosthesis according to claim 4 characterized in that:
   the adhesive has a weight content of about 17.5 to 30% of hydrophobic oleogel.

13. The adhesive for a dental prosthesis according to claim 1, wherein Vaseline is added in an amount up to 5% by weight and the paraffin and amorphous polyethylene are provided in a ratio of from 93:7 to 97:3.

14. The adhesive of claim 5, wherein the subsequent stirring takes place for at least three and a half hours.

15. A method of preparing an adhesive for a dental prosthesis comprising:

heating a paraffin having a viscosity of about 200 Pa.s to a temperature in excess of 120° C., adding and dissolving therein an amorphous polyethylene, stirring the mixture, cooling the mixture to a temperature below room temperature at a cooling rate of at least 50° C. to form a hydrophobic oleogel; and, ultimately mixing the hydrophobic oleogel with an adhesive component.

* * * * *

UNITED STATES PATENT AND TRADEMARK OFFICE
CERTIFICATE OF CORRECTION

PATENT NO. : 5,858,379
DATED : 12 January 1999
INVENTOR(S) : Mira REUSS and Rainer KNOLLMAN It is certified that error appears in the above-identified patent and that said Letters Patent is hereby corrected as shown below:

At column 8, line 2, delete "50°C" and insert --5°C--.

Signed and Sealed this

Eighth Day of June, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO. : 5,858,379
DATED : 12 January 1999
INVENTOR(S) : Mira REUSS and Rainer KNOLLMAN It is certified that error appears in the above-indentified patent and that said Letters Patent is hereby corrected as shown below:

On the title page, at "[73] Assignee:", delete "Reckitt & Colman Inc., Wayne, N.J." and insert --Kukident GmbH, Weinheim, Germany--.

Signed and Sealed this

Twenty-eighth Day of September, 1999

Attest:

Q. TODD DICKINSON

Attesting Officer

Acting Commissioner of Patents and Trademarks